United States Patent [19]

Mikulicz et al.

[11] 4,137,274

[45] Jan. 30, 1979

[54] PROCESS FOR MOTOR FUEL PRODUCTION BY OLEFIN POLYMERIZATION

[75] Inventors: Michael Z. Mikulicz, Palatine; Vance P. Burton, Arlington Heights, both of Ill.

[73] Assignee: UPO Inc., Des Plaines, Ill.

[21] Appl. No.: 750,348

[22] Filed: Dec. 13, 1976

Related U.S. Application Data

[63] Continuation-in-part of Ser. No. 588,105, Jun. 18, 1975, abandoned, which is a continuation-in-part of Ser. No. 475,686, Jun. 3, 1974, abandoned.

[51] Int. Cl.$^2$ ................................................. C07C 3/16
[52] U.S. Cl. ........................ 260/683.15 C; 260/671 R; 260/671 P; 260/671 C

[58] Field of Search ........... 260/671 R, 671 C, 671 P, 260/683.15 C

[56]  References Cited

U.S. PATENT DOCUMENTS 3,527,823  9/1970  Jones ................................. 260/671 P

*Primary Examiner*—C. Davis
*Attorney, Agent, or Firm*—James R. Hoatson, Jr.; John F. Spears, Jr.; William H. Page, II

[57]  ABSTRACT

A process for the production of motor fuel by the polymerization of aliphatic $C_3$ and $C_4$ mono-olefins wherein a small amount of a liquid aromatic hydrocarbon is passed through the polymerization zone to remove polymers. By-product alkylated aromatic hydrocarbons are retained in the motor fuel product as high octane components.

4 Claims, No Drawings

PROCESS FOR MOTOR FUEL PRODUCTION BY OLEFIN POLYMERIZATION

CROSS-REFERENCE TO RELATED APPLICATIONS

This application is a Continuation-In-Part of our prior now abandoned application Ser. No. 588,105 filed June 18, 1975 which was a Continuation-In-Part of our then copending application Ser. No. 475,686 filed June 3, 1974 and now abandoned.

FIELD OF THE INVENTION

The invention relates to a hydrocarbon conversion process. More specifically, the invention relates to a process for the catalytic polymerization of olefinic hydrocarbons and to the production of automotive fuel by the polymerization of olefinic hydrocarbons through the use of a solid phosphoric acid catalyst.

PRIOR ART

The polymerization of olefins to form motor fuel was one of the early catalytic processess for the production of automotive fuels and is still practiced commercially. The process is described in U.S. Pat. No. 2,234,177. The preferred type of catalytst, commonly referred to as a solid phosphoric acid catalyst, is described in this reference and other references including U. S. Pat No. 3,050,472; 3,050,473 and 3,132,109.

It has been recognized in the art that when a fixed bed of solid phosphoric acid catalysts are used for the polymerization of normally gaseous olefins an undesirable layer of polymers gradually forms on the surface of the catalyst. This eventually increases the pressure drop through the catalyst bed or lowers the activity of the catalyst to the extent that the process cannot be economically operated. In U.S. Pat. No. 2,658,933 a process is presented which is carried out in a slurry-type reactor. This type of reactor is filled with an agitated slurry or suspension of finely divided catalyst particles in a dense, fluid hydrocarbon phase. A slurry-type reactor system has the unique problem of the catalyst particles agglomerating and sinking to the bottom of the reactor due to polymer formation. The solution to this problem presented in this reference is to selectively remove the agglomerated or highly polymer-coated catalyst from the reaction zone, wash this catalyst with a suitable solvent, and then return it to the reaction zone. The preferred solvents are alkylaromatic hydrocarbons having a single ring structure with alkyl side-chains of no more than two carbon atoms length or other low boiling aromatic hydrocarbons. The reference is directed to the production of gasoline boiling range polymers.

In describing the prior art this reference refers to another application, presumably directed to another slurry type reactor system, in which polymer formation is taught to be prevented by washing the catalyst continuously or intermittently with an aromatic solvent. This procedure is described as disadvantageous. The reference then states that it is not feasible to include an aromatic solvent or the like along with the reactants in the reaction zone to prevent agglomerization since such materials enter into the reaction and produce undesirable side products.

U.S. Pat. No. 2,658,059 describes another process for the production of gasoline from low molecular weight olefins, such as ethylene. This process utilizes two reactors which are alternated between on-stream usage for polymerization and a polymer extraction and regeneration step. The preferred catalyst contains nickel and cobalt supported on activated charcoal. The polymer extraction operation comprises washing the catalyst bed which has been removed from operation with a solvent, such as a $C_6$ to $C_{12}$ aromatic hydrocarbon.

BRIEF SUMMARY OF THE INVENTION

The invention provides a process for the production of motor fuel by the polymerization of normally gaseous olefins in which polymer formation on the catalyst bed is controlled or essentially prevented. A broad embodiment of the invention comprises the steps of admixing about 0.5 to about 5.0 wt.% of an aromatic hydrocarbon having a boiling point below 400° F. into a feed stream comprising normally gaseous aliphatic olefins; contacting the feed stream with a polymerization catalyst in a polymerization zone maintained at polymerization-promoting conditions including a pressure sufficient to maintain over 50 vol.% of the added aromatic hydrocarbon as a liquid, and effecting the polymerization of a large portion of the normally gaseous olefins; withdrawing an effluent stream from the polymerization zone comprising polymers formed from the normally gaseous olefins, the aromatic hydrocarbon, and an alkylated aromatic hydrocarbon formed by the reaction of a smaller portion of the normally gaseous olefins and the aromatic hydrocarbon; and recovering from the effluent stream a motor fuel product comprising the polymers formed from the normally gaseous olefins, the aromatic hydrocarbon and the alkylated aromatic hydrocarbon.

DETAILED DESCRIPTION

In the early 1930's processes for the polymerization of light olefins were developed to make economic use of the light olefinic by-products of the then widely practiced thermal processing operations. These polymerization processes employed a catalyst and are often referred to as catalytic condensation processes. The basic product of these processes was a high octane motor fuel. This basic application was latter extended to the processing of propylene and butylenes derived from fluid catalytic cracking units to produce higher molecular weight olefins and later yet to the alkylation of aromatics with light olefins. The process became established as an important octane generator in the refinery and by the early 1950's more than 200 such units were in operation. This indicates that those skilled in the art are familiar with the construction and operation of these units.

Olefin polymerization has been largely replaced in recent years by sulfuric acid and HF alkylation for producing motor fuel from light olefins. However, the process has retained significant commercial importance, particularly where the isobutane needed for these alkylation units is either unavailable or expensive. The typican feed streams to the unit are propylene and/or butylene-containing streams derived from a fluid catalytic cracking unit, a thermal cracking unit or a gas concentration unit. The feed stream preferably contains at least 50 vol.% olefins, but feed streams with lower olefin concentrations may also be processed. These olefins are to be normally gaseous olefins, a term which is intended to refer to those olefinic acyclic hydrocarbons having a boiling point below 70° F. at a pressure of 1 atmosphere absolute. The feed should be substantially free of sulfur and nitrogen compounds.

The production of motor fuel by the polymerization of these normally gaseous olefins has traditionally suffered from the deposition of a polymer coating upon the catalyst. This has two undesirable results. First, it increases the pressure drop through the polymerization zone. This by itself can force the premature shut-down of the process. For instance, a high pressure drop may cause damage to the polymerization zone reactor internals and increases the utility costs of the process. Shut-downs caused by a high pressure drop across the catalyst bed are referred to as premature since the majority of the catalyst is still sufficiently active to be used in the process. The second undesirable result of polymer formation is a decrease in catalyst activity. It is an objective of this invention to provide a process for the production of a motor fuel by the polymerization of normally gaseous olefins in which the deposition of polymers on the catalyst bed is either reduced or eliminated.

The subject process may be applied to any type of solid polymerization catalyst which is effective in producing gasoline boiling range polymers from normally gaseous olefins. It may therefore be applied to a catalyst containing nickel and cobalt supported on an activated charcoal base as described in the previously cited U.S. Pat. No. 2,658,059. However, the process is preferably performed with an SPA (solid phosphoric acid) type catalyst. An SPA catalyst is one which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15-30% of the catalyst, with the remainder being the phosphoric acid. The additive may comprise about 3-20% of the total carrier material. Variations from this such as lower phosphoric acid content are however possible. Further details as to the composition and production of SPA catalysts may be obtained from U.S. Pat. Nos. 3,050,472; 3,050,473 and 3,132,109 and from other references.

The catalyst is disposed within a reaction or polymerization zone. Either a tubular or chamber type reactor structure may be used. In a tubular reactor the catalyst is placed in relatively small diameter tubes which are surrounded by a water jacket to remove the heat liberated by the exothermic reaction. Steam generated in this manner can be used to preheat the feed. In a chamber-type reactor the reactants flow through a series of large diameter catalyst beds. The temperature of the reactants is controlled by recycling relatively inert hydrocarbons which act as a heat sink or by the use of a quench between the catalyst beds. The quench material is the same as that used as the recycle stream, and both methods of temperature control may be used simultaneously. The different catalyst beds are preferably contained within a single, cylindrical, vertically oriented vessel, and the feed stream preferably enters the top of the polymerization zone. A chamber-type reactor containing about five catalyst beds is preferred.

The polymerization zone is maintained at polymerization-promoting conditions. These conditions include a superatmospheric pressure sufficient to keep at least 50 vol. % of the aromatic hydrocarbon-containing solvent stream in a liquid phase. This minimum required pressure will vary with the temperature which is used. A broad range of suitable pressures is from about 50 psig. to about 1000 psig., with a preferred pressure range being from 100 to 500 psig. The temperature may vary from about 250° F. to about 500° F. Steam or water may be fed into the polymerization zone to maintain the desired water content in the catalyst.

In the preferred embodiment SPA catalyst is utilized in a chamber type polymerization zone to form gasoline having a boiling point range within the temperatrue range of 110° F. to 420° F. as determined by the appropriate ASTM distillation method. The feed stream is commingled with a recycle stream comprising propane and butane which is used as a temperature controlling diluent. It is then admixed with an aromatic hydrocarbon-containing solvent stream, heat exchanged with the polymerization zone effluent, further heated and passed into the top of the polymerization zone. Additional amounts of the propane/butane coolant similar to the recycle stream are added between each of the catalyst beds.

The effluent of the polymerization zone is heat exchanged against the feed stream and then flashed. The resulting flash drum vapor stream is cooled to form a liquid stream used as part of the recycle stream. The flash drum liquid stream is passed into an intermediate point of a fractionation column utilized as a stabilizer. The overhead vapors of this column are condensed to form reflux and a net overhead liquid stream. This overhead liquid stream is combined with the liquid stream of flash drum condensate to form the total recycle stream. Low boiling polymers may be returned to polymerization zone in this manner to effect their further polymerization. The motor fuel product is recovered as the bottoms stream of the fractionation column. This description of the preferred embodiment is not intended to withdraw from the scope of the invention those other embodiments described herein or which are the result of reasonable modification. For instance, the flash drum liquid stream may be directed into a fractionation zone of a different process unit for the recovery of the motor fuel product.

The aromatic hydrocarbons are added to the feed stream at the minimum rate which will prevent the buildup of a polymer layer on the majority of the catalyst bed. An alternate way of stating this is that the rate of flow of the aromatic-containing liquid should be sufficient to prevent any sizable increase in the pressure drop across the reactor. The adequacy of the addition rate can therefore be easily monitored by observation of the pressure drop across the catalyst bed. This minimum rate may be temporarily exceeded to remove additional amounts of polymer buildup. The stream containing the aromatic hydrocarbons should be substantially free of sulfur and nitrogen compounds and have an end boiling point below about 400° F. In a more limited embodiment, the end boiling point of this stream is below 350° F. to ensure the boiling point of alkylated aromatic hydrocarbons produced in the polymerization zone will be acceptable as gasoline components. This stream may contain other types of hydrocarbons besides aromatic hydrocarbons. The aromatic hydrocarbons can be contained in any available refinery stream, but it preferably has a research clear octane number over 80 and contains over 50 vol.% aromatics. These aromatics may be benzene, xylene, toluene, isopropylbenzene, etc. The aromatics may be contained in a relatively pure aromatic stream, but these streams are normally more valuable as petrochemical feedstocks. A suitable aromatic-containing stream is the stabilized effluent of a catalytic reforming process. Another potential source for the aromatic hydrocarbons is the extract stream of a liquid-liquid extraction process adapted for the recovery of aromatic hydrocarbons. The rate of addition of the aromatic hydrocarbons is preferably between about 0.5 to about 5.0 wt.% of the olefin-containing feed stream.

It is part of the inventive concept that the aromatic hydrocarbons will be at least partly alkylated within the polymerization or reaction zone. This is contrary to the prior art which teaches that the products of the alkylation reaction are undesirable in a motor fuel polymerization process. In the subject process the alkylation of a light aromatic hydrocarbon, such as benzene or toluene, produces an alkylated aromatic hydrocarbon having a higher octane number than the light aromatic hydrocarbon. As long as its boiling point is not above the maximum allowed for the motor fuel product, there is no necessity to remove it from the motor fuel. To help ensure this favorable result the end boiling point of the aromatic hydrocarbons should be lower than that desired for the motor fuel product by about 20 Fahrenheit degrees or more and is preferably below about 350° F. If available, the preferred aromatic hydrocaron-containing stream is one which is destined to be used as a gasoline or a gasoline blending component as this usage as the solvent stream would be only a detour, and all of this stream would be recovered in the product motor fuel. The alkylation performed in the subject process is promoted by the SPA catalyst in essentially the same manner as this catalyst is used in alkylation processes such as described in U.S. Pat Nos. 3,437,708 and 3,487,119. No more than 10 mol.% of the olefins in the feed should be consumed in the alkylation reaction, and preferably less than 5% should be used in this reaction.

The invention has two other advantages. First, it produces a relatively free flowing catalyst bed which is easier to remove when the catalyst must eventually be replaced. Second, it allows longer usage of the catalyst and reduces the problem of disposing of the spent catalyst in an environmentally accepted manner.

We claim as out invention:

1. A process for the production of motor fuel which comprises the steps of:
   (a) admixing into a feed stream comprising normally gaseous olefins about 0.5 to about 5.0 wt. %, based on the feed stream, of an aromatic hydrocarbon having a boiling point below 400° F.;
   (b) contacting the resultant mixture with a polymerization catalyst in a reaction zone maintained at polymerizationpromoting conditions including a pressure sufficient to maintain at least 50 vol. % of the added aromatic hydrocarbon in a liquid phase, effecting as the principal reaction in the process the polymerization of a large portion of the normally gaseous olefins to form polymers having boiling points within the range of 110° F. to 420° F., and also effecting the alkylation of a portion of the aromatic hydrocarbon with a smaller second portion of the normally gaseous olefins to form a high octane alkylated aromatic hydrocarbons;
   (c) withdrawing an effluent stream from the reaction zone comprising the polymers, the aromatic hydrocarbon and the alkylated aromatic hydrocarbon; and,
   (d) recovering from the effluent stream a motor fuel product comprising the polymers, the aromatic hydrocarbon and the alkylated aromatic hydrocarbon.

2. The process of claim 1 wherein the method of recovering the motor fuel product comprises the steps of: cooling the effluent stream; flashing the effluent stream to form a flash vapor stream and a flash liquid stream; and fractionating the flash liquid stream to produce a fractionation column bottoms stream comprising the motor furel product and having a boiling point range within the range of about 110° F. to about 420° F.

3. The process of claim 1 wherein the polymerization catalyst is a solid phosphoric acid catalyst.

4. The process of claim 1 wherein the end boiling point of the aromatic hydrocarbon is below 350° F.

* * * * *